United States Patent [19]

Herweh

[11] 4,104,301
[45] Aug. 1, 1978

[54] SYNTHESIS OF SULFONYL SEMICARBAZIDES

[75] Inventor: John E. Herweh, Lancaster, Pa.

[73] Assignee: Armstrong Cork Company, Lancaster, Pa.

[21] Appl. No.: 770,016

[22] Filed: Feb. 18, 1977

Related U.S. Application Data

[63] Continuation of Ser. No. 675,452, Apr. 9, 1976, abandoned, which is a continuation-in-part of Ser. No. 490,040, Jul. 19, 1974.

[51] Int. Cl.$^2$ ............................................. C07C 133/02
[52] U.S. Cl. ........................................ 260/554; 521/89
[58] Field of Search ........................................ 260/554

[56] References Cited

U.S. PATENT DOCUMENTS

| 3,152,176 | 10/1964 | Hunter | 260/554 |
| 3,235,519 | 2/1966 | Hunter | 260/554 |
| 3,344,182 | 9/1967 | Amidon | 260/554 |
| 3,357,865 | 12/1967 | Davis et al. | 136/137 |
| 3,903,157 | 9/1975 | Hunter | 260/554 |
| 3,933,909 | 1/1976 | Herwey | 260/554 |

OTHER PUBLICATIONS

Hirooka, Chem. Abstracts, 1963, col. 11254g.

*Primary Examiner*—Arthur P. Demers

[57] ABSTRACT

A new synthetic route to sulfonyl semicarbazides (sulfonyldiazanecarboxamides) and sulfonyl-1,2-diazanedicarboxyamide wherein a substituted 1,2-diazenedicarboxamide is reacted with a salt of a sulfinic acid.

8 Claims, No Drawings

SYNTHESIS OF SULFONYL SEMICARBAZIDES

CROSS-REFERENCE TO RELATED APPLICATION

This application is a continuation application of earlier filed application Ser. No. 675,452, filed Apr. 9, 1976, now abandoned, which is a continuation-in-part application of application Ser. No. 490,040, filed Jul. 19, 1974.

BACKGROUND OF THE INVENTION

1. Field of the Invention

This invention relates to a new synthesis for sulfonyl semicarbazides (sulfonyldiazanecarboxamides) and sulfonyl-1,2-diazanediacarboxyamide which are a class of thermally labile compounds some currently finding use as blowing agents.

2. Description of the Prior Art

Sulfonyl semicarbazides are presently produced by reacting the corresponding sulfonyl hydrazide with a source of cyanic acid as exemplified in U.S. Pat. No. 3,152,176-Hunter. Another method for synthesizing sulfonyl semicarbazides is disclosed in assignee's copending application Ser. No. 490,039, filing date July 19, 1974, entitled A Method for Producing Sulfonyl Semicarbazides by John E. Herweh.

SUMMARY OF THE INVENTION

The process involved is the reaction of sulfinic acid salts with alpha-carbonyl azo compounds in particular with 1,1' azobisformamide and other substituted 1,2-diazenecarboxamides. The yields of the sulfonyl semicarbazides are high, in some cases essentially quantitative, and offer economical advantages over presently used preparatory routes for which the yields described in the literature are considerably smaller.

According to this invention there is provided a process for the manufacture of sulfonyl dicarboxamides of the formula

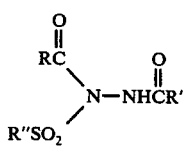

wherein R and R' may be the same or different and are $C_1$ to $C_8$ alkylamino, di $C_1$ to $C_8$ alkylamino, phenylamino, diphenylamino, $C_1$ to $C_8$ alkyl substituted phenylamino, di $C_1$ to $C_8$ alkyl substituted phenylamino, naphthylamino or dinaphthylamino; R" is selected from the group consisting of $C_1$ to $C_8$ alkyl, phenyl, $C_1$ to $C_8$ alkyl substituted phenyl and naphthyl, which comprises reacting either in water or in an inert aprotic dipolar solvent a diazenedicarboxamide of the formula R'CN=NCR with an organosulfinic acid salt of the formula $R"SO_2M$ wherein R, R' and R" is defined above and M is potassium, sodium, zinc or ammonium and recovering the sulfonyl dicarboxamide.

Also, according to this invention there is provided sulfonyl dicarboxamides of the formula

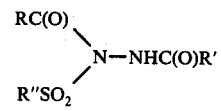

wherein R and R' are the same or different and are selected from the group consisting of $C_1$ to $C_8$ alkylamino, di $C_1$ to $C_8$ alkylamino, phenylamino, diphenylamino, $C_1$ to $C_8$ alkyl substituted phenylamino, naphthylamino, and dinaphthylamino; and R" is selected from the group consisting of $C_1$ to $C_8$ alkyl, phenyl, $C_1$ to $C_8$ alkyl substituted phenyl and naphthyl.

DESCRIPTION OF THE PREFERRED EMBODIMENT

When dimethyl sulfoxide solutions of equimolar amounts of 1,1' azobisformamide or other 1,2-diazenecarboxamides and zinc, sodium, potassium or ammonium salts of organosulfinic acids are combined at room temperature, an immediate reaction occurs, as evidenced by the rapid disappearance of the yellow-orange color associated with diazenedicarboxamide. Addition of the reaction mixtures to water causes the corresponding sulfonyldiazanecarboxamides and sulfonyl-1,2-diazanedicarboxyamide (sulfonyl semicarbazides) to precipitate as white solids in high yields and in a relative pure state. It should be noted that hereafter the term sulfonyl semicarbazides will be referred to in the more generally acceptable nomenclature as sulfonyldiazane carboxamides. Similarly, the older term sulfonyl-1,2-hydrazodicarboxamide is hereinafter referred to as the sulfonyl-1,2-diazanedicarboxamide. This reaction is greatly facilitated by solvation of the particular metal cation of the sulfinate salt in dimethyl sulfoxide or other similar dipolar aprotic solvent.

The reaction of 1,2-substituted diazenedicarboxamides with salts of organic sulfinic and may be expressed by the following general formula:

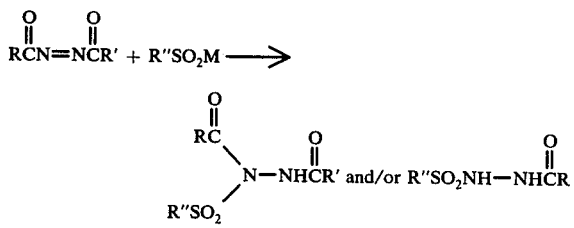

where R" signifies $C_1$ to $C_8$ alkyl, phenyl, $C_1$ to $C_8$ alkyl substituted phenyl or naphthyl, M is selected from the group consistng of zinc, sodium, potassium or ammonium, R and R' are the same or different and are $NH_2$, $C_1$ to $C_8$ alkylamino, di $C_1$ to $C_8$ alkylamino, phenylamino, diphenylamino, substituted phenylamino, di substituted diphenylamino, naphthyl amino or dinaphthylamino.

Examples of 1,2-diazenedicarboxamides which can be used for the purpose of this invention are:
1,1' azobisformamide (1,2-diazenedicarboxamide)
N,N-dimethyl 1,2 diazenedicarboxamide
N,N-diethyl 1,2 diazenedicarboxamide
N,N-dipropyl 1,2 diazenedicarboxamide
N,N-dibutyl 1,2 diazenedicarboxamide
N,N-dioctyl 1,2 diazenedicarboxamide
N,N-diphenyl 1,2-diazenedicarboxamide
N,N-di(4-methylphenyl) 1,2-diazenedicarboxamide N,N'-dimethyl-1,2-diazenedicarboxamide
N,N'-diethyl-1,2-diazenedicarboxamide
N,N'-dibutyl-1,2-diazenedicarboxamide
N,N'-dioctyl-1,2-diazenedicarboxamide
N,N'-diphenyl-1,2-diazenedicarboxamide
N,N'-di(4-methylphenyl)-1,2-diazenedicarboxamide
N,N'-dinaphthyl-1,2-diazenedicarboxamide The organosulfinic acid salt will have the formula R"$SO_2$M where R" is alkyl having from 1 to 8 carbon atoms, phenyl, lower alkyl substituted phenyl, or naphthyl, and M is zinc, sodium, potassium or ammonium.

Examples of sulfinic acid salts which can be used for the purpose of this invention are:
zinc bis (p-toluenesulfinate)
zinc bis (benzenesulfinate)
sodium p-toluenesulfinate
sodium benzenesulfinate
ammonium p-toluenesulfinate
zinc dipentanesulfinate
potassium xylenesulfinate The reactions are carried out in dipolar aprotic solvents inert to the starting ingredients. The role of such solvent is to dissolve, at least in part, one or more of the reactants without effecting any change in chemical composition of the reactant species. Solvents of this type found useful in this invention include tetrahydrothiophene 1,1-dioxide, tetramethyl urea, hexamethyl phosphoryl triamide, dimethyl sulfoxide, dimethylformamide and the like. Mixtures of these solvents are also useful in reacting this invention. The two most commonly used are dimethylsulfoxide and dimethylformamide. The former is the most preferred dipolar aprotic solvent for use in these reactions.

Water may also be used in these systems when it does not react with either of the two reactants and dissolves at least in part one of them. For instance, a water suspension of 1,1' azobisformamide can be reacted with a water solution of sodium benzenesulfinate or sodium p toluenesulfinate which results in an alkaline reaction mixture that requires neutralization to completely separate out the sulfonyl semicarbazide. Similarly, when a dipolar aprotic solvent suspension of substituted 1,2-diazenedicarboxamide is reacted with a dipolar aprotic solvent solution of sodium p-toluenesulfinate, neutralization of the resulting alkaline reaction mixture is required to recover the sulfonyl semicarbazide completely.

The reaction should be carried out in a temperature range from approximately 20° C. to 80° C. and preferably in the range of 45° C. to 50° C. when water is the solvent of choice, and 25° C. to 35° C. when an aprotic solvent is used.

The concentration of the reactants in the inert solvent should be in the range of 5% to 50% by weight of the solvent and preferably in the range of from 8% to 12% by weight of the solvent when water is used and from 5% to 50% by weight when an aprotic solvent is utilized. Generally, the concentration of the reactant will depend on the so of the reactant in the solvent.

The reaction may be carried out in any convenient manner utilizing suitable vessels or containers. One of the outstanding advantages of the present process is its simplicity, requiring mere mixing of the reactive solutions, and separating out the product.

In many cases the yields of sulfonyl semicarbazides are near quantitative and the materials are analytically pure after appropriate washing and drying.

The following examples illustrate several embodiments of the invention.

EXAMPLE 1

General Procedure for Reaction of 1,2-diazenedicarboxamides with Metal Organosulfinates in Dimethyl Sulfoxide 1,2-diazenedicarboxamide (e.g. 1,1' azobisformamide, 0.01 mol) and the metal organosulfinate (molar amount depending on metal cation) are dissolved in a suitable amount of dimethyl sulfoxide (typically 25 ml per 0.01 mol for both 1,1' azobisformamide and the sulfinate). When the two solutions are combined, the yellow to orange color due to 1,2-diazenedicarboxamide fades almost immediately. The color is usually completely discharged after several minutes. Typically, the reaction mixture is left at room temperature overnight prior to workup.

The relatively clear, colorless reaction mixture is added to excess water (about 300 ml per 50 ml of reaction mixture) and cooled to ice both temperatures. The white solid precipitate is filtered, washed with fresh cold water and dried in a vacuum (in presence of $P_2O_5$).

The procedure followed when dimethyl formamide is used, as the solvent is identical to that described above.

The results from a number of reactions are summarized in the following table:

Reaction of 1,2-diazenedicarboxamide (0.01 Mol) with Metal Organosulfinates in Dipolar Aprotic Solvents

| Metal Organo-sulfinte | Mol | Reaction Time, Minutes | Solvent[a] (ml) | Sulfonyl-diazane-carboxamide Mol | % Yield |
|---|---|---|---|---|---|
| | | | Dimethyl Sulfoxide | | |
| Zn bis (p-toluene-sulfinate) | .005 | Approx. 3 min. | 65[b] | .0088 | 88 |
| Zn bis (p-toluene-sulfinate) | .005 | Approx. 3 min. | 50 | .0090 | 90 |
| Zn bis (benzene-sulfinate)[c] | .005 | Approx. 3 min. | 50 | .0086 | 86 |
| Na p-toluene-sulfinate | .01 | Approx. 3 min. | 40 | .0081 | 81 |
| | | | Dimethyl Formamide | | |
| Zn bis (benzene-sulfinate) | .005 | Approx. 3 min. | 75 | .0079 | 79 |

[a]Total volume
[b]t-butyl alcohol (20 ml) also present
[c]Dihydrate

EXAMPLE 2

General Procedure for Reaction of 1,2-diazenedicarboxamides with Metal Organosulfinates in Water A solution of sodium organosulfinate (0.05 mol) in 50 ml of water is added rapidly to a stirred suspension of 1,1' azobisformamide (0.05 mol) in 100 ml of water. No apparent reaction occurs and the reaction mixture is quickly heated to 45° C. to 50° C.

The reaction mixture is maintained at 45° C. to 50° C. for a varied period of time until the suspended solid phase became white. After cooling to room temperature, the alkaline reaction mixture is neutralized with 3N hydrochloric acid and the filer-cake is washed thoroughly with water and dried in a vacuum (in presence of $P_2O_5$). The reaction product was identified as sulfonyl diazanecarboxamides by elemental analysis, molecular weight, melting point, infrared and nuclear magnetic resonance spectroscopy.

The results from a number of reactions are summarized in the following table:

| Reaction of 1,1'Azobisformamide (0.05 Mol) with Sodium Organosulfinates (0.05 Mol) in Water | | | |
|---|---|---|---|
| | | Sulfonyl Semicarbazide | |
| No. | Sodium Organosulfinate | Reaction Time, Minutes | Mol | % Yield |
| 1 | benzenesulfinate | 90 | .046 | 92 |
| 2 | p-toluenesulfinate | 75 | .049 | 98 |
| 3 | p-toluenesulfinate | 45 | .050 | 99 |

EXAMPLE 3

General Procedure for the Reaction of Substituted Diazenedicarboxamides with Metal Organosulfinates The substituted diazenedicarboxamides (0.01 mol), dissolved in 25 ml of $Me_2SO$, were combined with solutions of the sulfinate (0.01 mol) in 25 ml of $Me_2SO$ and the reaction mixtures were worked up in a manner similar to that described for 1,2-diazenedicarboxamide (Example 1). Addition of the reaction mixtures to water gave weakly basic solutions. In the case of the N,N'-diethyl- and N,N,N',N'-tetramethyldiazenedicarboxamides the basic solutions remained clear, but solid reaction products precipitated upon acidification (see the following table). When added to water, reaction mixtures containing the substituted N-phenyl derivatives gave milky basic reaction mixtures; acidifications gave the products shown in the table.

In the case of N,N'-diphenyl-1,2-diazenedicarboxamide the crude reaction product was resolved into its two components by treatment with cold aqueous 5% sodium hydroxide. 1-p-toluenesulfonyl-N,N-diphenyl-1,2-diazanedicarboxamide is insoluble in the cold alkali and can be purified by repeated recrystallization from benzene. The aqueous alkali solubles were acidified to precipitate the I component; repeated recrystallization from acetic acid afforded analytically pure product.

The results obtained from these reactions are summarized below.

$$\overset{O}{\underset{\|}{R}}CN=NC\overset{O}{\underset{\|}{R'}} + R''SO_2M \longrightarrow$$

$$\underset{R''SO_2}{\overset{RC\overset{O}{\|}}{\diagdown}}N-NHCR' \text{ and/or } R''SO_2NH-NHCR$$

I        II where $R''SO_2M$ = sodium p-toluene sulfinate

| R' | R | Product Type[a] | % Yield | MP° C. |
|---|---|---|---|---|
| EtNH | EtNH | II | 39 | 199–200° DEC[b] |
| Me₂N | Me₂N | I | 77 | 197–198° DEC[c] |
| H₂N | Ph₂N | II | 98 | 186–188° DEC[d] |
| PhN | PhN | I & II | 33 & 27 | 180–182.5 DEC & |

| R' | R | Product Type[a] | % Yield | MP° C. |
|---|---|---|---|---|
| | | | | 210–211 DEC |

[a]Satisfactory elemental analyses and molecular weight determinations were recorded for all compounds.
[b]Recrystallized from chloroform
[c]Recrystallized from 1:4 carbon tetrachloride:chloroform
[d]Recrystallized from abs. alcohol

What is claimed is:

1. A process for the manufacture of sulfonyl dicarboxamides of the formula $$\underset{R''SO_2}{\overset{RC\overset{O}{\|}}{\diagdown}}N-NHCR'\overset{O}{\underset{\|}{}}$$

wherein R and R' may be the same or different and are $C_1$ to $C_8$ alkylamino, di $C_1$ to $C_8$ alkylamino, phenylamino, diphenylamino, $C_1$ to $C_8$ alkyl substituted phenylamino, di $C_1$ to $C_8$ alkyl substituted phenylamino, naphthylamino or dinaphthylamino; R" is selected from the group consisting of $C_1$ to $C_8$ alkyl, phenyl, $C_1$ to $C_8$ alkyl substituted phenyl and naphthyl, which comprises reaction in an inert aprotic dipolar solvent a diazenedicarboxamide of the formula $$R'\overset{O}{\underset{\|}{C}}N=NC\overset{O}{\underset{\|}{R}}$$

with an organosulfinic acid salt of the formula $R''SO_2M$ wherein R, R' and R" is defined above and M is potassium, sodium, zinc or ammonium and recovering the sulfonyl dicarboxamide.

2. The process of claim 1 wherein said inert aprotic dipolar solvent is selected from the group consisting essentially of dimethylsulfoxide, dimethylformamide, tetrahydro-1,1dioxide, tetramethyl urea, hexamethylphosphoryl triamide and mixtures thereof.

3. The process of claim 1 wherein R" is aromatic sulfinate selected from the group consisting essentially of phenyl, tolyl and naphthyl.

4. A process for the manufacture of sulfonyl dicarboxamides of the formula $$\underset{R''SO_2}{\overset{RC\overset{O}{\|}}{\diagdown}}N-NHCR'\overset{O}{\underset{\|}{}}$$

wherein R and R' may be the same or different and are $C_1$ to $C_8$ alkylamino, di $C_1$ to $C_8$ alkylamino, phenylamino, diphenylamino, $C_1$ to $C_8$ alkyl substituted phenylamino, di $C_1$ to $C_8$ alkyl substituted phenylamino, naphthylamino or dinaphthylamino; R" is selected from the group consisting of $C_1$ to $C_8$ alkyl, phenyl, $C_1$ to $C_8$ alkyl substituted phenyl and naphthyl, which comprises reacting in water a diazenedicarboxamide of the formula

with an organosulfinic acid salt of the formula R"SO$_2$M wherein R, R' and R" is defined above and M is potassium, sodium, zinc or ammonium and recovering the sulfonyl dicarboxamide.

5. Sulfonyl dicarboxamides of the formula

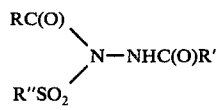

wherein R and R' are the same or different and are selected from the group consisting of C$_1$ to C$_8$ alkylamino, di C$_1$ to C$_8$ alkylamino, phenylamino, diphenylamino, C$_1$ to C$_8$ alkyl substituted phenylamino, naphthylamino, and dinaphthylamino; and R" is selected from the group consisting of C$_1$ to C$_8$ alkyl, phenyl, C$_1$ to C$_8$ alkyl substituted phenyl and naphthyl.

6. The 1,2-diazanedicarboxamide of claim 5 wherein R and R' are the same and are selected from the group consisting of dimethylamino and phenylamino.

7. The process of claim 4 wherein said inert aprotic dipolar solvent is selected from the group consisting essentially of dimethylsulfoxide, dimethylformamide, tetrahydrothiophene-1,1 dioxide, tetramethyl urea, hexamethylphosphoryl triamide and mixtures thereof.

8. The process of claim 4 wherein R" is aromatic group selected from the group consisting essentially of phenyl, tolyl and naphthyl.

* * * * *